(12) United States Patent
Albarran et al.

(10) Patent No.: US 7,534,819 B2
(45) Date of Patent: May 19, 2009

(54) COMPOSITIONS AND METHODS FOR INTRACELLULAR DELIVERY OF BIOTINYLATED CARGO

(75) Inventors: Brian Albarran, Seattle, WA (US); Patrick S. Stayton, Seattle, WA (US); Richard To, Bellevue, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 11/150,588

(22) Filed: Jun. 10, 2005

(65) Prior Publication Data

US 2006/0281677 A1    Dec. 14, 2006

(51) Int. Cl.
*A61K 47/42*    (2006.01)
*A61K 47/48*    (2006.01)
*A61K 38/00*    (2006.01)

(52) U.S. Cl. .................. 514/772; 514/788.2; 514/2; 424/185.1; 530/350; 530/300; 530/815

(58) Field of Classification Search .................. 435/7.5, 435/7.1; 530/367, 350; 514/2; 424/486
See application file for complete search history.

(56) References Cited

U.S. PATENT DOCUMENTS

| | | | | |
|---|---|---|---|---|
| 6,835,393 | B2 * | 12/2004 | Hoffman et al. | ............ 424/450 |
| 6,881,825 | B1 * | 4/2005 | Robbins et al. | ............ 530/327 |
| 2003/0219826 | A1 * | 11/2003 | Robbins et al. | ............... 435/7.1 |
| 2004/0209797 | A1 * | 10/2004 | Karas | ............................ 514/7 |
| 2005/0158373 | A1 * | 7/2005 | Szeto et al. | .................. 424/450 |

OTHER PUBLICATIONS

Mi et al. (2000) Characterization of a class of cationic peptides able to facilitate efficient protein transduction in vitro and in vivo. Mol. Ther. vol. 2, No. 4, pp. 339-347.*
Console e al. (2003) Antennapedia and HIV transactivator of transcription (TAT) "protein transduction domains" promote endocytosis of high molecular weight cargo upon binding to cell surface glycosaminoglycans. J. Biol. Chem. vol. 278, issue, 37, 35 109-114.*
Shen et al. (2004) Evaluation of peptide-mediated transduction in human CD34+ cells. Hum. Gene Ther. vol. 15, No. 4, pp. 415-419.*
Kabouridis P. S. (2003) Biological applications of protein transduction technology. Trends Biotechnol. vol. 21, issue 11, pp. 498-503.*
Albarran et al. (2005) A TAT-streptavidin fusion protein directs uptake of biotinylated cargo into mammalian cells. Protein Eng. Des. Sel. vol. 18, issue 3, pp. 147-152.*
Soane et al. (2005) Inhibition of mitochondrial neural cell death pathways by protein transduction of Bcl-2 family proteins. J. Bioenerg. Biomembr. vol. 373, No. 3, pp. 179-190.*
Christie et al. (2003) Design strategies to improve soluble macromolecular delivery constructs, Adv. Drug Deliv. Rev., vol. 55, No. 3, pp. 421-437.*
Hyndman et al. (2004) HIV-1 Tat protein transduction domain peptide facilitates gene transfer in combination with cationic liposomes, J. Control Release, vol. 99, No. 3, pp. 435-444.*

Albarran, B., et al., "A TAT-Streptavidin Fusion Protein Directs Uptake of Biotinylated Cargo Into Mammalian Cells," *Protein Engineering, Design and Selection* 18(3):147-152, Mar. 2005.
Han, X., et al., "Membrane Structure and Fusion-Triggering Conformational Change of the Fusion Domain From Influenza Hemagglutinin," *Nature Structural Biology* 8(8):715-720, Aug. 2001.
Hong, F.D., and G.L. Clayman, "Isolation of a Peptide for Targeted Drug Delivery Into Human Head and Neck Solid Tumors," *Cancer Research* 60(23):6551-6556, Dec. 1, 2000.
Joliot, A., and A. Prochiantz, "Transduction Peptides: From Technology to Physiology," *Nature Cell Biology* 6(3):189-196, Mar. 2004.
Langedijk, J.P.M., et al., "New Transport Peptides Broaden the Horizon of Applications for Peptidic Pharmaceuticals," *Molecular Diversity* 8(2):101-111, Jun. 2004.
Li, W., et al., "GALA: A Designed Synthetic pH-Responsive Amphipathic Peptide With Applications in Drug and Gene Delivery," *Advanced Drug Delivery Reviews* 56(7):967-85, Apr. 23, 2004.
Mastrobattista, E., et al., "Functional Characterization of an Endosome-Disruptive Peptide and Its Application in Cytosolic Delivery of Immunoliposome-Entrapped Proteins," *Journal of Biological Chemistry* 277(30):27135-27143, Jul. 26, 2002.
Morris, M.C., et al., "A Peptide Carrier for the Delivery of Biologically Active Proteins Into Mammalian Cells," *Nature Biotechnology* 19:1173-1176, Dec. 2001.
Mortlock, A., et al., "Suppression of Gene Expression by a Cell-Permeable Tet Repressor," *Nucleic Acids Research* 31(23):e152 (7 pages), Dec. 1, 2003.
Plank, C., et al., "The Influence of Endosome-Disruptive Peptides on Gene Transfer Using Synthetic Virus-Like Gene Transfer Systems," *Journal of Biological Chemistry* 269(17):12918-12924, Apr. 29, 1994.
Säälik, P., et al., "Protein Cargo Delivery Properties of Cell-Penetrating Peptides. A Comparative Study," *Bioconjugate Chemistry* 15(6):1246-1253, Nov. 2004.
Zhao, M., and R. Weissleder, "Intracellular Cargo Delivery Using Tat Peptide and Derivatives," *Medicinal Research Reviews* 24(1):1-12, Jan. 2004.
Barka, T., et al., "Transduction of TAT-HA-β-Galactosidase Fusion Protein Into Salivary Gland-Derived Cells and Organ Cultures of the Developing Gland, and Into Rat Submandibular Gland In Vivo," *Journal of Histochemistry & Cytochemistry* 48(11):1453-1460, 2000.

(Continued)

*Primary Examiner*—Jon P Weber
*Assistant Examiner*—Samuel W Liu
(74) *Attorney, Agent, or Firm*—Christensen O'Connor Johnson Kindness PLLC

(57) ABSTRACT

The invention provides compositions for intracellular delivery of biotinylated cargo. The compositions comprise a complex formed between (a) a fusion protein comprising a protein transduction domain linked to streptavidin and (b) a biotinylated cargo for intracellular delivery. In some embodiments, the protein transduction domain comprises the protein transduction domain of the Human Immunodeficiency Virus type 1 (HIV-1) TAT protein. The complex may further comprise a biotinylated endosomal releasing polymer, such as a poly (propylacrylic acid) polymer. The invention also provides methods for obtaining intracellular delivery of biotinylated cargo and methods for obtaining cytoplasmic delivery of biotinylated cargo.

10 Claims, 2 Drawing Sheets

OTHER PUBLICATIONS

Bennett, R.P., and B. Dalby, "Protein Delivery Using VP22," *Nature Biotechnology 20*:20, Jan. 2002.

Cao, G., et al., "In Vivo Delivery of Bcl-xL Fusion Protein Containing the TAT Protein Transduction Domain Protects Against Ischemic Brain Injury and Neuronal Apoptosis," *Journal of Neuroscience 22*(13):5423-5431, Jul. 1, 2002.

Derossi, D., et al., "Cell Internalization of the Third Helix of the Antennapedia Homeodomain Is Receptor-Independent," *Journal of Biological Chemistry 271*(30):18188-18193, Jul. 26, 1996.

Derossi, D., et al., "The Third Helix of Antennapedia Homeodomain Translocates Through Biological Membranes," *Journal of Biological Chemistry 269*(14):10444-10450, Apr. 8, 1994.

Elliott, G., and P. O'Hare, "Intercellular Trafficking and Protein Delivery by a Herpesvirus Structural Protein," *Cell 88*:223-233, Jan. 24, 1997.

Fawell, S., et al., "Tat-Mediated Delivery of Heterologous Proteins Into Cells," *Cell Biology 91*:664-668, Jan. 1994.

Fittipaldi, A., et al., "Cell Membrane Lipid Rafts Mediate Caveolar Endocytosis of HIV-1 Tat Fusion Proteins," *Journal of Biological Chemistry 278*(36) 34141-34149, Sep. 5, 2003.

Frankel, A.D., and C.O. Pabo, "Cellular Uptake of the Tat Protein From Human Immunodeficiency Virus," *Cell 55*:1189-1193, Dec. 23, 1988.

Green, M., and P.M. Loewenstein, "Autonomous Functional Domains of Chemically Synthesized Human Immunodeficiency Virus Tat *Trans*-Activator Protein," *Cell 55*:1179-1188, Dec. 23, 1988.

Hughes, J.A., et al., "Evaluation of Adjuvants That Enhance the Effectiveness of Antisense Oligodeoxynucleotides," *Pharmaceutical Research 13*(3):404-410, 1996.

Klumb, L.A., et al., "Energetic Roles of Hydrogen Bonds at the Ureido Oxygen Binding Pocket in the Streptavidin-Biotin Complex," *Biochemistry 37*(21):7657-7663, May 26, 1998.

Lackey, C.A., et al., "A Biomimetic pH-Responsive Polymer Directs Endosomal Release and Intracellular Delivery of an Endocytosed Antibody Complex," *Bioconjugate Chemistry 13*:996-1001, 2002.

Lackey, C.A., et al., "Hemolytic Activity of pH-Responsive Polymer-Streptavidin Bioconjugates," *Bioconjugate Chemistry 10*:401-405, 1999.

Leifert, J.A., and J.L. Whitton, "'Translocatory Proteins' and 'Protein Transduction Domains': A Critical Analysis of Their Biological Effects and the Underlying Mechanisms," *Molecular Therapy 8*(1):13-20, Jul. 2003.

Lin, Y.-Z., et al., "Inhibition of Nuclear Translocation of Transcription Factor NF-κb by a Synthetic Peptide Containing a Cell Membrane-Permeable Motif and Nuclear Localization Sequence," *Journal of Biological Chemistry 270*(24):14255-14258, Jun. 16, 1995.

Murthy, N., et al., "The Design and Synthesis of Polymers for Eukaryotic Membrane Disruption," *Journal of Controlled Release 61*:137-143, 1999.

Nagahara, H., et al., "Transduction of Full-Length TAT Fusion Proteins Into Mammalian Cells: TAT-p27$^{Kip\ 1}$ Induces Cell Migration," *Nature Medicine 4*(12):1449-1452, Dec. 1998.

Pawlak, M., et al., "Template-Assembled Melittin: Structural and Functional Characterization of a Designed, Synthetic Channel-Forming Protein," *Protein Science 3*:1788-1805, 1994.

Pooga, M., et al., "Cell Penetration by Transportan," *The FASEB (Federation of American Societies for Experimental Biology) Journal 12*:67-77, 1998.

Schwarze, S.R., et al., "Protein Transduction: Unrestricted Delivery Into All Cells?" *trends in Cell Biology 10*:290-295, Jul. 2000.

Snyder, E.L., and S.F. Dowdy, "Protein/Peptide Transduction Domains: Potential to Deliver Large DNA Molecules Into Cells," *Current Opinion in Molecular Therapeutics 3*(2):147-152, 2001.

Vivès, et al., "A Truncated HIV-1 Tat Protein Basic Domain Rapidly Translocates Through the Plasma Membrane and Accumulates in the Cell Nucleus," *Journal of Biological Chemistry 272*(25):16010-16017, Jun. 20, 1997.

Wadia, J.S., et al., "Transducible TAT-HA Fusogenic Peptide Enhances Escape of TAT-Fusion Proteins After Lipid Raft Macropinocytosis," *Nature Medicine 10*(3):310-315, Mar. 2004.

* cited by examiner

SEQUENCE LISTING

<160> NUMBER OF SEQ ID NOS: 43

<210> SEQ ID NO 1
<211> LENGTH: 11
<212> TYPE: PRT
<213> ORGANISM: Human Immunodeficiency Virus-1

-continued

<400> SEQUENCE: 1

Tyr Gly Arg Lys Lys Arg Arg Gln Arg Arg
1               5                   10

<210> SEQ ID NO 2
<211> LENGTH: 16
<212> TYPE: PRT
<213> ORGANISM: Drosophila Melanogaster

<400> SEQUENCE: 2

Arg Gln Ile Lys Ile Trp Phe Gln Asn Arg Arg Met Lys Trp Lys Lys
1               5                   10                  15

<210> SEQ ID NO 3
<211> LENGTH: 21
<212> TYPE: PRT
<213> ORGANISM: Bufo Gargarizans

<400> SEQUENCE: 3

Thr Arg Ser Ser Arg Ala Gly Leu Gln Phe Pro Val Gly Arg Val His
1               5                   10                  15

Arg Leu Leu Arg Lys
            20

<210> SEQ ID NO 4
<211> LENGTH: 26
<212> TYPE: PRT
<213> ORGANISM: Homo Sapiens

<400> SEQUENCE: 4

Gly Trp Thr Leu Asn Ser Ala Gly Tyr Leu Leu Gly Lys Ile Asn Lys
1               5                   10                  15

Ala Leu Ala Ala Leu Ala Lys Lys Ile Leu
            20                  25

<210> SEQ ID NO 5
<211> LENGTH: 18
<212> TYPE: PRT
<213> ORGANISM: Artificial Sequence
<220> FEATURE:
<223> OTHER INFORMATION: Model Amphipathic Peptide

<400> SEQUENCE: 5

Lys Leu Ala Leu Lys Leu Ala Leu Lys Ala Leu Lys Ala Ala Leu Lys
1               5                   10                  15

Leu Ala

<210> SEQ ID NO 6
<211> LENGTH: 16
<212> TYPE: PRT
<213> ORGANISM: Artificial Sequence
<220> FEATURE:
<223> OTHER INFORMATION: Synthetic

<400> SEQUENCE: 6

Ala Ala Val Ala Leu Leu Pro Ala Val Leu Leu Ala Leu Leu Ala Pro
1               5                   10                  15

<210> SEQ ID NO 7
<211> LENGTH: 5
<212> TYPE: PRT
<213> ORGANISM: Artificial Sequence
<220> FEATURE:

<223> OTHER INFORMATION: Synthetic

<400> SEQUENCE: 7

Val Pro Met Leu Lys
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic

<400> SEQUENCE: 8

Pro Met Leu Lys Glu
1               5

<210> SEQ ID NO 9
<211> LENGTH: 28
<212> TYPE: PRT
<213> ORGANISM: Artificial Sequence
<220> FEATURE:
<223> OTHER INFORMATION: Synthetic

<400> SEQUENCE: 9

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 10
<211> LENGTH: 18
<212> TYPE: PRT
<213> ORGANISM: Artificial Sequence
<220> FEATURE:
<223> OTHER INFORMATION: Synthetic

<400> SEQUENCE: 10

Leu Leu Ile Ile Leu Arg Arg Arg Ile Arg Lys Gln Ala His Ala His
1               5                   10                  15

Ser Lys

<210> SEQ ID NO 11
<211> LENGTH: 20
<212> TYPE: PRT
<213> ORGANISM: Artificial Sequence
<220> FEATURE:
<223> OTHER INFORMATION: Synthetic

<400> SEQUENCE: 11

Lys Glu Thr Trp Trp Glu Thr Trp Trp Thr Glu Trp Ser Gln Pro Lys
1               5                   10                  15

Lys Lys Arg Lys
            20

<210> SEQ ID NO 12
<211> LENGTH: 18
<212> TYPE: PRT
<213> ORGANISM: Artificial Sequence
<220> FEATURE:
<223> OTHER INFORMATION: Synthetic

<400> SEQUENCE: 12

Arg Gly Gly Arg Leu Ser Tyr Ser Arg Arg Phe Ser Thr Ser Thr
1               5                   10                  15

```
Gly Arg

<210> SEQ ID NO 13
<211> LENGTH: 15
<212> TYPE: PRT
<213> ORGANISM: Artificial Sequence
<220> FEATURE:
<223> OTHER INFORMATION: Synthetic

<400> SEQUENCE: 13

Ser Asp Leu Trp Glu Met Met Met Val Ser Leu Ala Cys Gln Tyr
1               5                   10                  15

<210> SEQ ID NO 14
<211> LENGTH: 12
<212> TYPE: PRT
<213> ORGANISM: Artificial Sequence
<220> FEATURE:
<223> OTHER INFORMATION: Synthetic

<400> SEQUENCE: 14

Thr Ser Pro Leu Asn Ile His Asn Gly Gln Lys Leu
1               5                   10

<210> SEQ ID NO 15
<211> LENGTH: 7
<212> TYPE: PRT
<213> ORGANISM: Human Immunodeficiency Virus-1

<400> SEQUENCE: 15

Lys Arg Arg Gln Arg Arg Arg
1               5

<210> SEQ ID NO 16
<211> LENGTH: 7
<212> TYPE: PRT
<213> ORGANISM: Human Immunodeficiency Virus-1

<400> SEQUENCE: 16

Arg Lys Lys Arg Arg Gln Arg
1               5

<210> SEQ ID NO 17
<211> LENGTH: 8
<212> TYPE: PRT
<213> ORGANISM: Human Immunodeficiency Virus-1

<400> SEQUENCE: 17

Arg Lys Lys Arg Arg Gln Arg Arg
1               5

<210> SEQ ID NO 18
<211> LENGTH: 4
<212> TYPE: PRT
<213> ORGANISM: Artificial Sequence
<220> FEATURE:
<223> OTHER INFORMATION: Synthetic

<400> SEQUENCE: 18

Arg Arg Arg Arg
1

<210> SEQ ID NO 19
<211> LENGTH: 5
<212> TYPE: PRT
```

-continued

```
<213> ORGANISM: Artificial Sequence
<220> FEATURE:
<223> OTHER INFORMATION: Synthetic

<400> SEQUENCE: 19

Arg Arg Arg Arg Arg
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic

<400> SEQUENCE: 20

Arg Arg Arg Arg Arg
1               5

<210> SEQ ID NO 21
<211> LENGTH: 16
<212> TYPE: PRT
<213> ORGANISM: Artificial Sequence
<220> FEATURE:
<223> OTHER INFORMATION: Synthetic

<400> SEQUENCE: 21

Arg Arg Arg Arg Arg Arg Arg Arg Arg Arg Arg Arg Arg Arg Arg Arg
1               5                   10                  15

<210> SEQ ID NO 22
<211> LENGTH: 16
<212> TYPE: PRT
<213> ORGANISM: Saccharomyces Cerevisiae

<400> SEQUENCE: 22

Thr Arg Arg Asn Lys Arg Asn Arg Ile Gln Glu Gln Leu Asn Arg Lys
1               5                   10                  15

<210> SEQ ID NO 23
<211> LENGTH: 18
<212> TYPE: PRT
<213> ORGANISM: Bacteriophage phi-21

<400> SEQUENCE: 23

Thr Ala Lys Thr Arg Tyr Lys Ala Glu Glu Ala Glu Leu Ile Ala Glu
1               5                   10                  15

Arg Arg

<210> SEQ ID NO 24
<211> LENGTH: 22
<212> TYPE: PRT
<213> ORGANISM: Bacteriophage lambda

<400> SEQUENCE: 24

Met Asp Ala Gln Thr Arg Arg Arg Glu Arg Arg Ala Glu Lys Gln Ala
1               5                   10                  15

Gln Trp Lys Ala Ala Asn
            20

<210> SEQ ID NO 25
<211> LENGTH: 15
<212> TYPE: PRT
<213> ORGANISM: Feline Herpes Virus
```

```
<400> SEQUENCE: 25

Arg Arg Arg Arg Asn Arg Thr Arg Arg Asn Arg Arg Val Arg
1               5                   10                  15

<210> SEQ ID NO 26
<211> LENGTH: 6
<212> TYPE: PRT
<213> ORGANISM: Artificial Sequence
<220> FEATURE:
<223> OTHER INFORMATION: Synthetic

<400> SEQUENCE: 26

Arg Arg Arg Arg Arg Arg
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic

<400> SEQUENCE: 27

Arg Arg Arg Arg Arg Arg
1               5

<210> SEQ ID NO 28
<211> LENGTH: 19
<212> TYPE: PRT
<213> ORGANISM: Brome Mosaic Virus

<400> SEQUENCE: 28

Lys Met Thr Arg Ala Gln Arg Arg Ala Ala Ala Arg Arg Asn Arg Trp
1               5                   10                  15

Thr Ala Arg

<210> SEQ ID NO 29
<211> LENGTH: 13
<212> TYPE: PRT
<213> ORGANISM: HTLV-II

<400> SEQUENCE: 29

Thr Arg Arg Gln Arg Thr Arg Arg Ala Arg Arg Asn Arg
1               5                   10

<210> SEQ ID NO 30
<211> LENGTH: 17
<212> TYPE: PRT
<213> ORGANISM: Human Immunodeficiency Virus-1

<400> SEQUENCE: 30

Thr Arg Gln Ala Arg Arg Asn Arg Arg Arg Arg Trp Arg Glu Arg Gln
1               5                   10                  15

Arg

<210> SEQ ID NO 31
<211> LENGTH: 13
<212> TYPE: PRT
<213> ORGANISM: Human Immunodeficiency Virus-1

<400> SEQUENCE: 31

Gly Arg Lys Lys Arg Arg Gln Arg Arg Arg Pro Pro Gln
1               5                   10
```

```
<210> SEQ ID NO 32
<211> LENGTH: 9
<212> TYPE: PRT
<213> ORGANISM: Human Immunodeficiency Virus-1

<400> SEQUENCE: 32

Arg Arg Arg Gln Arg Arg Lys Lys Arg
1               5

<210> SEQ ID NO 33
<211> LENGTH: 9
<212> TYPE: PRT
<213> ORGANISM: d-Human Immunodeficiency Virus-1

<400> SEQUENCE: 33

Arg Lys Lys Arg Arg Gln Arg Arg Arg
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic

<400> SEQUENCE: 34

Arg Arg Arg Arg Arg Arg
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic

<400> SEQUENCE: 35

Arg Arg Arg Arg Arg Arg Arg
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic

<400> SEQUENCE: 36

Arg Arg Arg Arg Arg Arg Arg
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic

<400> SEQUENCE: 37

Arg Arg Arg Arg Arg Arg Arg Arg
1               5

<210> SEQ ID NO 38
<211> LENGTH: 8
<212> TYPE: PRT
<213> ORGANISM: Artificial Sequence
```

```
<220> FEATURE:
<223> OTHER INFORMATION: Synthetic

<400> SEQUENCE: 38

Arg Arg Arg Arg Arg Arg Arg Arg
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic

<400> SEQUENCE: 39

Arg Arg Arg Arg Arg Arg Arg Arg Arg
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic

<400> SEQUENCE: 40

Arg Arg Arg Arg Arg Arg Arg Arg Arg
1               5

<210> SEQ ID NO 41
<211> LENGTH: 30
<212> TYPE: PRT
<213> ORGANISM: Artificial Sequence
<220> FEATURE:
<223> OTHER INFORMATION: Synthetic

<400> SEQUENCE: 41

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30

<210> SEQ ID NO 42
<211> LENGTH: 69
<212> TYPE: DNA
<213> ORGANISM: Artificial Sequence
<220> FEATURE:
<223> OTHER INFORMATION: Synthetic

<400> SEQUENCE: 42
acggggaatc atatgtacgg tcgtaaaaaa cgtcgtcagc gtcgtcgtgg tgctgaagct     60
ggtatcacc                                                             69

<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43
ttcgaaccgt gaccggcagc                                                 20
```

US 7,534,819 B2

COMPOSITIONS AND METHODS FOR INTRACELLULAR DELIVERY OF BIOTINYLATED CARGO

STATEMENT OF GOVERNMENT LICENSE RIGHTS

This invention was made with government support under Grant Nos. EB00252, DK49655, and CA55596 awarded by the National Institutes of Health. The government has certain rights in the invention.

FIELD OF THE INVENTION

The present invention relates to compositions and methods for delivering molecules of interest across biological membranes.

BACKGROUND OF THE INVENTION

Efficient translocation across biological membranes is crucial for the delivery of therapeutic and diagnostic agents. In addition to drug delivery, there are many potential in vitro applications in areas such as drug discovery and laboratory assays that could benefit from improved intracellular delivery of biomolecules and macromolecular cargo. Protein transduction domains (PTDs; also referred to as cell penetrating peptides) have attracted considerable interest in the drug delivery field for their ability to translocate across biological membranes. The PTDs are relatively short sequences that confer this apparent translocation activity to proteins and other macromolecular cargo to which they are conjugated, complexed or fused (Derossi et al. (1994) *J. Biol. Chem.* 269:10444-50; Fawell et al. (1994) *Proc. Natl. Acad. Sci. U.S.A.* 91:664-68; Elliott & O'Hare (1997) *Cell* 88:223-33; Schwarze et al. (2000) *Trends Cell Biol.* 10:290-5; Snyder & Dowdy (2001) *Curr. Opin. Mol. Ther.* 3:147-52; Bennett et al. (2002) *Nat. Biotechnol.* 20:20). The translocation mechanism is still unclear, but studies with PTDs have suggested that translocation is an energy-independent and nonreceptor-mediated event and that most cell types can be targeted (Derossi et al. (1994) *J. Biol. Chem.* 269:10444-50; Derossi et al. (1996) *J. Biol. Chem.* 271:18188-93; Vives et al. (1997) *J. Biol. Chem.* 272:16010-7; Nagahara et al. (1998) *Nat. Med.* 4:1449-52; Schwarze et al. (2000) *Trends Cell Biol.* 10:290-5). However, some recent studies have suggested that the PTDs direct highly efficient cellular uptake through regular pinocytotic mechanisms (Leifert et al. (2002) *Gene Ther.* 9:1422-8; Fittipaldi et al. (2003) *J. Biol. Chem.* 278:34141-9; Leifert & Lindsay Whitton (2003) *Mol. Ther.* 8:13-20; Lundberg et al. (2003) *Mol. Ther.* 8:143-50; Richard et al. (2003) *J. Biol. Chem.* 278:585-90; Vives et al. (2003) *Curr. Protein Pept. Sci.* 4:125-32).

Linkage of PTDs to molecules of interest has been used extensively for directing the intracellular delivery of an assortment of cargo, including DNA, liposomes and macromolecules. For the delivery of protein cargo, for example, the protein may be covalently linked to a PTD in a fusion protein. There is a need in the art for methods and compositions that facilitate the linkage of PTDs to cargo. The present invention addresses this and other needs.

SUMMARY OF THE INVENTION

In one aspect, the invention provides compositions for intracellular delivery of biotinylated cargo. The compositions comprise a complex formed between (a) a fusion protein comprising a protein transduction domain linked to streptavidin and (b) a biotinylated cargo for intracellular delivery. In some embodiments, the protein transduction domain comprises the protein transduction domain of the Human Immunodeficiency Virus type 1 (HIV-1) TAT protein. The cargo may be any molecule that can be introduced into cells by using a PTD, such as, for example, a protein, a nucleic acid, a small molecules, particles, and liposomes. The complexes may further comprise a biotinylated endosomal releasing polymer. In some embodiments, the endosomal releasing polymer is a poly(propylacrylic acid) polymer.

In another aspect, the invention provides methods for obtaining intracellular delivery of biotinylated cargo. The methods comprise the step of exposing cells to a complex comprising (a) a fusion protein comprising a protein transduction domain linked to streptavidin to obtain intracellular delivery of the biotinylated cargo and (b) a biotinylated cargo. In some embodiments, the protein transduction domain comprises the protein transduction domain of the Human Immunodeficiency Virus type 1 (HIV-1) TAT protein. In some embodiments, the complex further comprises a biotinylated endosomal releasing polymer, such as a poly(propylacrylic acid) polymer.

A further aspect of the invention provides methods for obtaining cytoplasmic delivery of a biotinylated cargo. The methods comprise the step of exposing cells to a complex comprising (a) a fusion protein comprising a protein transduction domain linked to streptavidin to obtain cytoplasmic delivery of the biotinylated cargo, (b) a biotinylated cargo, and (c) a biotinylated endosomal release polymer.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
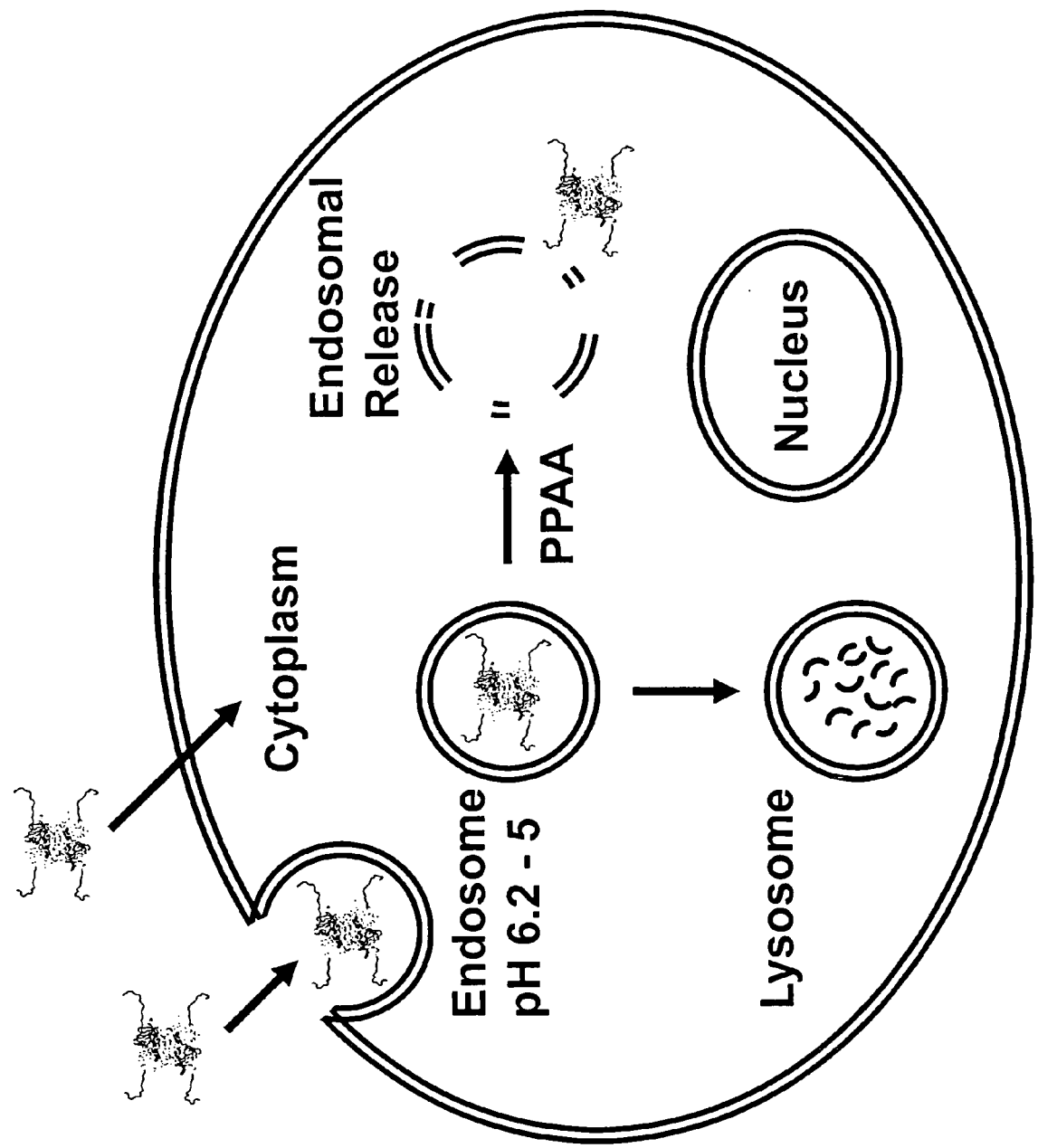
FIG. 1 shows a diagram illustrating cellular uptake and trafficking of TAT-streptavidin (TAT-SA) fusion protein. Although the cellular uptake mechanism remains unclear, a possible pinocytotic mechanism is diagramed here. PPAA: poly(propylacrylic) acid.

One aspect of the invention provides compositions comprising a complex formed between (a) a fusion protein comprising a protein transduction domain linked to streptavidin and (b) a biotinylated cargo for intracellular delivery. The plasma membrane of cells consists of a lipid bilayer that presents a barrier to entry of macromolecules into the cell. As used herein, the term "protein transduction domain" or "PTD" refers to a domain (for example, a peptide or other polymer) that is able to confer membrane translocation activity to proteins and other macromolecular cargo to which it is linked. PTDs are sometimes referred to as cell penetrating peptides (CPPs). A large variety of PTDs have been characterized, including, but not limited to, naturally occurring PTDs, artificial PTDs, and PTDs selected from random libraries (see, e.g., Joliot & Prochiantz (2004) *Nat. Cell Biol.* 6(3):189-96; Zhao & Weissleder (2003) *Med Res. Rev.* 24(1):

1-12; Säälik et al. (2004) *Bioconj. Chem.* 15:1246-1253; each of which is herein incorporated by reference in its entirety). A list of exemplary PTDs suitable for use in the compositions of the invention is provided in Tables 1 and 2. Other examples of PTDs that may be used in the compositions of the invention include endosomal releasing polymers, such as GALA, as described further below.

In some embodiments, the PTD used in the complexes of the invention is a PTD of the human immunodeficiency virus (HIV-1) TAT protein. One of the most well-studied PTDs is the highly cationic 11 amino acid residue PTD (YGRKKRRQRRR, SEQ ID NO:1) from the HIV-1 TAT protein (Frankel & Pabo (1988) *Cell* 55:1189-93; Green & Loewenstein (1988) *Cell* 55:1179-88). In-frame fusion proteins containing the TAT sequence were shown to direct cellular uptake of proteins that retained their activity intracellularly (Nagahara et al. (1998) *Nat. Med.* 4:1449-52; Kwon et al. (2000) *FEBS Lett.* 485:163-7; Becker-Hapak et al. (2001) *Methods* 24:247-256; Jo et al. (2001) *Nat. Biotechnol.* 19:929-33; Xia et al. (2001) *Nat. Biotechnol.* 19:640-4; Cao et al. (2002) *J. Neurosci.* 22:5423-31; Joshi et al. (2002) *Genesis* 33:48-54; Kabouridis et al. (2002) *J. Immunol.* 169:2587-93; Peitz et al. (2002) *Proc. Natl. Acad. Sci. U.S.A.* 99:4489-94). Subsequently, a diverse collection of over 60 full-length proteins with functional domains from 15 to 120 kDa have been engineered to date. Various studies employing TAT-fusion methodologies have demonstrated transduction in a variety of both primary and transformed mammalian and human cell types, including peripheral blood lymphocytes, diploid fibroblasts, keratinocytes, bone marrow stem cells, osteoclasts, HeLa cells, and Jurkat T-cells (Fawell et al. (1994) *Proc. Natl. Acad. Sci. U.S.A.* 91:664-68; Nagahara et al. (1998) *Nat. Med.* 4:1449-52; Gius et al. (1999) *Cancer Res.* 59:2577-80; Vocero-Akbani et al. (1999) *Nat. Med.* 5:29-33; Vocero-Akbani et al. (2000) *Methods Enzymol.* 322:508-21; Vocero-Akbani et al. (2001) *Methods Enzymol.* 332:36-49; Becker-Hapak et al. (2001) *Methods* 24:247-256). Furthermore, in vivo intracellular delivery by injection of a TAT-b-gal fusion has been demonstrated (Schwarze et al. (1999) *Science* 285:1569-72; Barka et al. (2000) *J. Histochem. Cytochem.* 48:1453-60).

Other naturally occurring PTDs include the homeodomain of the *Drosophila melanogaster* protein *Antennapedia* (Lindsay (2002) *Curr. Op. Pharmacol.* 2:587-94; Derossi et al. (1994) *J. Biol. Chem.* 269:10444-50), HSV-1 VP22 (Bennett et al. (2002) *Nat. Biotechnol.* 20:20), and Buforin II (Park et al. (2000) *Proc. Natl. Acad. Sci. U.S.A.* 97:8245-50).

In addition, many artificial PTDs have been designed to mimic and/or enhance the translocating properties of known PTDs, based on consideration of parameters such as electrostatic and hydrophobic properties or secondary structure (Wender et al. (2000) *Proc. Natl. Acad. Sci. U.S.A.* 97:13003-8; Futaki et al. (2001) *J. Biol. Chem.* 276:5836-40). Some artificial PTDs have been discovered when small peptides with membrane-interacting properties were tested for translocation (see, e.g., Lin et al. (1995) *J. Biol. Chem.* 270:14255-8). An exemplary artificial PTD is transportan (Pooga et al. (1998) *FASEB J.* 12:67-77; Soomets et al. (2000) *Biochim. Biophys. Acta* 1467:165-76). Moreover, synthetic PTDs such as polylysine, polyarginine, and polyhistidine (which can be positively charged based on the pH of the formulation) have been used. An exemplary synthetic PTD is polyarginine (6-15 amino acids).

Further PTDs have been selected from random libraries, for example, from phage display libraries (Hong & Clayman (2000) *Cancer Res.* 60:6551-6; Gao et al. (2002) *Bioorg. Med. Chem.* 10:4057-65), and a number of new PTDs are being characterized (Elmquist et al. (2001) *Exp. Cell Res.* 269:237-44; Lundberg et al. (2002) *Biochem. Biophys. Res. Commun.* 299:85-90).

TABLE 1

Examples of Commonly-Used PTDs (Joliot & Prochiantz (2004) Nat. Cell Biol. 6(3): 189-96)

| PTD | Sequence | Reference |
|---|---|---|
| TAT | YGRKKRRQRRR (SEQ ID NO:1) | 1 |
| Antennapedia (Penetratin) | RQIKIWFQNRRMKWKK (SEQ ID NO:2) | 2 |
| Buforin II | TRSSRAGLQFPVGRVHRLLRK (SEQ ID NO:3) | 3 |
| Transportan | GWTLNSAGYLLGKINKALAALAKKIL (SEQ ID NO:4) | 5 |
| MAP (Model Amphipathic Peptide) | KLALKLALKALKAALKLA (SEQ ID NO:5) | 6 |
| K-FGF | AAVALLPAVLLALLAP (SEQ ID NO:6) | 7 |
| Ku70 | VPMLK (SEQ ID NO:7) | 8 |
|  | PMLKE (SEQ ID NO:8) |  |
| Prion | MANLGYWLLALFVTMWTDVGLCKKRPKP (SEQ ID NO:9) | 9 |
| pVEC | LLIILRRRIRKQAHAHSK (SEQ ID NO:10) | 10 |
| Pep-1 | KETWWETWWTEWSQPKKKRKV (SEQ ID NO:11) | 11 |
| SynB1 | RGGRLSYSRRRFSTSTGR (SEQ ID NO:12) | 12 |
| Pep-7 | SDLWEMMMVSLACQY (SEQ ID NO:13) | 13 |
| HN-1 | TSPLNIHNGQKL (SEQ ID NO:14) | 14 |

1 Frankel & Pabo (1988) Cell 55: 1189-93; Green & Loewenstein (1988) Cell 55: 1179-88
2 Derossi et al. (1994) J. Biol. Chem. 269: 10444-50
3 Park et al. (200) Proc. Natl Acad Sci. U.S.A. 97: 8245-50
4 Bennet et al. (2002) Nat. Biotechnol. 20: 20
5 Pooga et al. (1998) FASEB J. 12: 67-77; Soomets et al. (2000) Biochim. Biophyls. Acta 1467: 165-76
6 Oehlke et al. (1998) Biochim. Biophys. Acta 1414: 127-39
7 Lin et al. (1995) J. Biol. Chem. 270: 14255-8
8 Sawada et al. (2003) Nat. Cell. Biol. 5: 352-7
9 Lundberg et al. (2002) Biochem. Biophys. Res. Commun. 299: 85-90
10 Elmquist et al. (2001) Exp. Cell. Res. 269: 237-44
11 Morris et al. (2001) Nat. Biotechnol. 19: 1173-6
12 Rousselle et al. (2000) Mol. Pharmacol. 57: 679-86
13 Gao et al. (2002) Bioorg. Med. Chem. 10: 4057-65
14 Hong & Clayman (2000) Cancer Res. 60: 6551-6

Many studies have assessed and defined structural requirements of PTDs for efficient translocation, such as length, amino acid content, secondary structure, and alpha-helical content (Joliot & Prochiantz (2004) *Nat. Cell Biol.* 6(3):

189-96; Zhao & Weissleder (2003) *Med. Res. Rev.* 24(1):1-12). Many PTDs contain multiple arginines (Table 2). For example, the high density of guanidine groups plays a large role in the transmembrane activity of TAT (see, e.g., Zhao & Weissleder (2003) *Med. Res. Rev.* 24(1):1-12, and publications cited therein). Assays for identifying PTDs and optimizing their translocation activities are well known in the art (see, e.g., the assays described in the references cited in Tables 1 and 2). An exemplary method for assaying translocation activity of a PTD is described in EXAMPLE 1.

TABLE 2

Arginine/Guanidine-Rich PTDs (Zhao & Weissleder (2003) Med. Res. Rev. 24(1): 1-12)

| PTD | Sequence | Uptake Efficiency | Reference |
|---|---|---|---|
| HIV-1 $TAT_{51-57}$ | KRRQRRR (SEQ ID NO:15) | Low | 1 |
| HIV-1 $TAT_{49-55}$ | RKKRRQR (SEQ ID NO:16) | Low | 1 |
| HIV-1 $TAT_{49-56}$ | RKKRRQRR (SEQ ID NO:17) | Low | 1 |
| $Arg_4$ | RRRR (SEQ ID NO:18) | Low | 2 |
| $Arg_5$ | RRRRR (SEQ ID NO:19) | Medium | 1 |
| d-$Arg_5$ | rrrrr (SEQ ID NO:20) | Medium | 1 |
| Arg16 | RRRRRRRRRRRRRRRR (SEQ ID NO:21) | Medium | |
| Yeast $PRP6_{129-144}$ | TRRNKRNRIQEQLNRK (SEQ ID NO:22) | Medium | 2 |
| $\phi 21\ N_{12-29}$ | TAKTRYKAEEAELIAERR (SEQ ID NO:23) | Medium | 2 |
| $\lambda N_{1-22}$ | MDAQTRRRERRAEKQAQWKAAN (SEQ ID NO:24) | Medium | |
| FHV $coat_{35-49}$ | RRRRNRTRRNRRRVR (SEQ ID NO:25) | Medium | 2, 3 |
| $Arg_6$ | RRRRRR (SEQ ID NO:26) | Medium | 2 |
| d-$Arg_6$ | rrrrrr (SEQ ID NO:27) | Medium | 1 |
| BMV $Gag_{7-25}$ | KMTRAQRRAAARRNRWTAR (SEQ ID NO:28) | High | 2 |
| HTLV-II $Rex_{4-16}$ | TRRQRTRRARRNR (SEQ ID NO:29) | High | 2 |
| HIV-1 $Rev_{34-50}$ | TRQARRNRRRRWRERQR (SEQ ID NO:30) | High | 2, 3 |
| HIV-1 $TAT_{48-60}$ | GRKKRRQRRRPPQ (SEQ ID NO:31) | High | 3 |
| HIV-1 $TAT_{57-49}$ | RRRQRRKKR (SEQ ID NO:32) | High | 1 |
| d-HIV-1 $TAT_{49-57}$ | rkkrrqrrr (SEQ ID NO:33) | High | 1 |
| $Arg_7$ | RRRRRRR (SEQ ID NO:34) | High | 1 |
| d-$Arg_7$ | rrrrrrr (SEQ ID NO:35) | High | 1 |
| N-$Arg_7$ | RRRRRRR (SEQ ID NO:36) | High | 1 |

TABLE 2-continued

Arginine/Guanidine-Rich PTDs (Zhao & Weissleder
(2003) Med. Res. Rev. 24(1): 1-12)

| PTD | Sequence | Uptake Efficiency | Reference |
|---|---|---|---|
| $Arg_8$ | RRRRRRRR (SEQ ID NO:37) | High | 3 |
| $d-Arg_8$ | rrrrrrrr (SEQ ID NO:38) | High | 1 |
| Arg9 | RRRRRRRRR (SEQ ID NO:39) | High | 1 |
| d-Arg9 | rrrrrrrrr (SEQ ID NO:40) | High | 1 |
| Carbamate 9 | Guanidine-9-oligocarbamate | High | 4 |

1 Wender et al. (2000) Proc. Natl Acad. Sci. U.S.A. 97: 13003-8
2 Futaki et al. (2001) J. Biol. Chem. 276: 5836-40
3 Suzuki et al. (2002) J. Biol. Chem. 277: 2437-43
4 Wender et al. (2002) J. Am. Chem. Soc. 124: 13382-3

In the compositions of the invention at least one PTD is linked to streptavidin. The term "streptavidin" refers to any biotin-binding protein of the avidin family or a fragment thereof that is capable of binding biotin, including, but not limited to, avidin, streptavidin, and variants thereof, such as NeutrAvidin (Pierce Biotechnology) and CaptAvidin (Molecular Probes). In some embodiments, the PTD is linked to streptavidin by constructing an expression vector encoding an in-frame PTD-streptavidin fusion protein and expressing the fusion protein in suitable prokaryotic or eukaryotic cells. The term "PTD-streptavidin" fusion protein or "PTD-SA" refers to any fusion protein that retains both translocation activity of the PTD and the biotin-binding activity of streptavidin. The PTD may be located at either the amino or the carboxy terminus of the fusion protein, or at any other position of the fusion protein that does not destroy its biotin-binding activity. Methods for making an expression vector encoding a fusion and introducing such an expression vector into suitable cells for expression of the fusion protein are standard in the art (see, e.g., Sambrook et al. (1989) Molecular Cloning-A Laboratory Manual, Cold Spring Harbor Laboratory, Cold Spring Harbor, N.Y.). For example, a DNA molecule encoding a PTD may be linked to a DNA molecule encoding streptavidin using the polymerase chain reaction (PCR) and the resulting DNA molecule subsequently introduced into a suitable vector for expressing the fusion protein. The expression vector may be introduced into prokaryotic or eukaryotic cells for expression of the fusion protein, which may be isolated from the cells or their medium and further purified. An exemplary method for creating an expression vector encoding a PTD-streptavidin fusion protein, for expressing the PTD-streptavidin fusion protein in cells, and for purifying the expressed PTD-streptavidin fusion protein is provided in EXAMPLE 1.

The compositions of the invention further include a biotinylated cargo for intracellular delivery. As used herein, the term "cargo" includes any molecule that can be introduced into cells by using a PTD. It has been shown that PTDs may be used for intracellular delivery of proteins, nucleic acids, small molecules (e.g., low molecular weight pharmaceutical agents), and particles (see, e.g., Zhao & Weissleder (2003) Med Res. Rev. 24(1):1-12). For example, the HIV-1 TAT peptide has been used extensively for directing the intracellular delivery of an assortment of cargo, including DNA, liposomes and macromolecules. The efficiency of translocation of PTDs is generally very high, leading to uptake of the PTD and its cargo in cells of all cell types (Joliot & Prochiantz (2004) Nat. Cell Biol. 6(3):189-96). Moreover, the amount of PTD and cargo internalized can be efficiently controlled (Joliot & Prochiantz (2004) Nat. Cell Biol. 6(3):189-96). Thus, the term "cargo" includes, but is not limited to, proteins, nucleic acids, small molecules, and particles.

In the composition of the invention, the cargo is biotinylated. The term "biotinylated" or "biotinylation" refers to the addition to a cargo of one or more molecules of biotin, a biotin analog or derivative (e.g., diaminobiotin, 2-iminobiotin, biocytin, desthiobiotin, biotin-triethylene glycol, or a cleavable biotin analog), or any other reagent that is capable of binding to streptavidin. The cargo is biotinylated using methods that are standard in the art. For example, there are biotinylation reagents that take advantage of reactive groups that may be present on cargo molecules, including, but not limited to, amine, sulfhydryl, and carbohydrate groups. For example, N-hydroxysuccinimide (NHS) esters of biotin are the most popular type of biotinylation reagent for use with proteins. NHS-activated biotins react efficiently with primary amino groups ($-NH_2$) in pH 7-9 buffers to form stable amide bonds. Proteins generally have several primary amines in the side chain of lysine residues and the N-terminus of each polypeptide that are available as targets for labeling with NHS-activated biotin reagents. One of skill in the art will appreciate that cargo molecules may be modified to include a functional group that is reactive with a biotinylation reagent. Specialty biotinylation reagents are also available for biotinylating molecules that do not have a readily available functional group (see, e.g., Pierce Biotechnology; Molecular Probes).

In order to form complexes of the invention, the PTD-streptavidin fusion protein and at least one biotinylated cargo are incubated under suitable conditions for the formation of complexes. Complexes of PTD-SA and a biotinylated cargo of interest can be formed at varying molar ratios according to the following conditions (0<Biotinylated Cargo:PTD-SA≦4), where "Biotinylated Cargo:PTD-SA" refers to the molar ratio of biotinylated cargo per tetramer of PTD-SA. In embodiments in which there are four biotin binding sites on a single PTD-SA tetramer, the maximum molar ratio does not exceed four. In some embodiments, the actual number of molecules that are complexed to streptavidin or any streptavidin fusion may be less than four (for example, two) due to steric hindrance effects related to the effective size of the molecule. Suitable conditions for the formation of complexes between PTD-SA and biotinylated cargo include incubating the PTD-SA and cargo molecules for an appropriate period of time in a buffer that allows their native structure to be retained (i.e., neutral pH, non-denaturing conditions). In some embodiments, complexes are formed by incubating PTD-SA and biotinylated cargo together for 15 minutes at room temperature. An exemplary method for forming a complex between a streptavidin fusion protein and a biotinylated cargo is provided in EXAMPLE 1.

The complexes of the invention are efficiently delivered intracellularly, as described in EXAMPLE 1. Specifically, a TAT-streptavidin (TAT-SA) fusion protein was prepared that retains the ability to bind biotinylated cargo while directing their efficient cellular uptake. Fluorescence activated cell sorting (FACS) analysis and confocal microscopy characterization showed that TAT-SA is internalized by Jurkat T-cells and NIH 3T3 cells alone and when complexed to phycoerythrin, whereas the wild-type streptavidin is not. Additionally, biotinylated alkaline phosphatase is successfully internalized and retains its activity when complexed to TAT-SA and incubated with Jurkat T-cells.

In some embodiments, the complexes of the invention further comprise a biotinylated endosomal releasing polymer. Endosomes are membrane-bound phospholipid vesicles which function in intracellular trafficking and degradation of internalized proteins. Although complexes comprising PTD-streptavidin and biotinylated cargo are efficiently delivered into the cell, the complexes may be compartmentalized in vesicular compartments, rather than freely diffusing in the cytoplasmic compartment. To obtain cytoplasmic delivery, a biotinylated endosomal releasing polymer may be included in the complex. The term "endosomal releasing polymer" or "ERP" refers to a polymer that directs delivery of a complex including that polymer into the cytoplasm. Examples of endosomal releasing polymers include, but are not limited to, synthetic and natural pH-sensitive polymers that do not disrupt cell membranes at physiological pH but that disrupt the endosomal membrane at the pH range inside the endosomes; phospholipid bilayer disrupting polymers; and co-polymers of synthetic and/or natural pH-sensitive polymers and/or phospholipids bilayer disrupting agents, as described in U.S. Pat. No. 6,835,393, herein incorporated by reference, particularly from Col. 6, line 31, to Col. 9, line 26.

pH-sensitive polymers that may be used as ERPs are relatively hydrophilic and not membrane-disruptive at physiological pH (between pH 6.8 and pH 7.5; around pH 7.4 inside cells) and relatively hydrophobic and membrane-disruptive at the pH inside of the endosomes (between pH 5.0 and 6.5). Polymers that include multiple carboxylic acid groups (for example, polymers with more than 0.5 carboxylic acid groups per monomer on average) tend to be relatively hydrophilic at pH ranges in which the carboxylic acid groups are deprotonated (i.e. ionized), and tend to be relatively hydrophobic at pH ranges in which the carboxylic acid groups are protonated. The pKa for carboxylic acid groups is such that they tend to be protonated at the pH range present in the endosomes. Thus, random, block, and graft copolymers that include acrylate groups and alkyl substituted acrylate groups may be used as ERPs. In some embodiments, the ERPs are polymers containing ethylacrylic acid (EAA), propylacrylic acid (PAA), or butylacrylic acid (BAA). In some embodiments, the ERP is a homopolymer, such as, for example, a poly(propylacrylic acid) (PPAA) polymer.

Various peptides also disrupt endosomal membranes in a pH dependent manner. Exemplary peptides that may be used as ERPs include, but are not limited to, viral and bacterial peptides, such as influenza virus peptides; peptides that include or resemble the 23 amino terminal amino acid fusion domain of influenza virus hemagglutinin (Han et al. (2001) Nat. Struct. Biol. 8(8):715-20; Dowd et al. (2004) Nat. Med. 10(3):310-15), such as diNF-7 (Mastrobattista et al. (2002) J. Biol. Chem. 277(3):27135043); and peptides that mimic the manner in which viruses destabilize endosomal membranes in a pH-dependent manner, such as GALA (also known as EALA), which includes repeating glutamic acid-alanine-leucine-alanine blocks, and derivatives thereof (see, e.g., Plank et al. (1994) J. Biol. Chem. 17(269):12918-24; Hughes et al. (1996) Pharm Res. 13(3):404-10; Li et al. (2004) Adv. Drug Deliv. Rev. 56(7):967-85), and melittin or melittin derivatives (Pawlak et al. (1994) Prot. Sci. 3:1788-1805). In some embodiments, the ERP is GALA (WEAALAEALAEALAE-ALAEHLAEALEALAA, SEQ ID NO:41).

Polymers that disrupt the phospholipid bilayer at a lower pH may also be used as ERPs, for example polymers that include imidazole groups. The imidazole groups hydrolyze phosphate esters and carboxyl esters. Hydrolysis of lipids leads to the formation of lysophospholipids and fatty acids, both of which destabilize phospholipid bilayers and cause the disruption of cell membranes. Exemplary polymers that disrupt phospholipids bilayers include polymers including vinyl imidazole monomeric units and peptides containing histidine residues. For example, monomeric ethyl acrylic acid may be copolymerized with vinyl imidazole. At pH 7.4, this polymer will not interact with the lipid bilayer; however, at low pH this polymer will become hydrophobic and interact with the endosomal membrane, bringing the imidazole group close to the phospholipids, where it can hydrolyse them and cause membrane disruption.

Additional compounds have been demonstrated to overcome the endosomal barrier by mediating endosomal disruption through an alternative mechanism. Certain cationic polyamine polymers have been shown to provide pH-sensitive membrane disruption. Polyethylenimine (PEI), polyamidoamine (PAMAM), and poly(2-dimethylamino)ethyl methacrylate (p(DMAEMA)) all have higher order amines with pKas at or below pH 7.4, providing a means to buffer endosomal acidification. During a process termed the "proton sponge effect," protonation of the available cationic groups consumes incoming endosomal protons while the accumulation of counterions results in vesicular swelling and consequent endosomolysis.

ERPs may be biotinylated and assembled into the complexes of the invention as described above. In some embodiments, complexes of PTD-SA, biotinylated cargo, and biotinylated ERP are formed at 1:1:1 molar ratios. Alternatively, separate complexes of PTD-SA:biotinylated cargo and complexes of PTD-SA:biotinylated ERP may be assembled at varying molar ratios and co-delivered to cells. An exemplary method for the biotinylation of an ERP and its incorporation into a complex is described in EXAMPLE 1. Endosomal release and cytoplasmic delivery of fluorescently labeled TAT-SA complexes with biotinylated PPAA were shown by the diffuse distribution of fluorescent protein in the cytoplasm. Thus, PTD-streptavidin fusion proteins can be used to direct intracellular delivery of large biotinylated cargo to intracellular compartments and the presence of biotinylated PPAA in the complex can direct cytoplasmic delivery where desired.

Another aspect of the invention provides methods for obtaining intracellular delivery of biotinylated cargo. The methods comprise the step of exposing cells to a complex comprising (a) a fusion protein comprising a protein transduction domain linked to streptavidin to obtain intracellular delivery of the biotinylated cargo and (b) a biotinylated cargo. Suitable fusion proteins comprising a protein transduction domain (PTD) linked to streptavidin are as described above. In some embodiments, the PTD comprises the PTD of the HIV-1 TAT protein. Biotinylated cargo may be prepared and assembled into complexes with the PTD-streptavidin fusion protein as described above. In some embodiments, the complex further comprises an endosomal releasing polymer. Suitable endosomal releasing polymers are as described above. In some embodiments, the endosomal releasing polymer is a biotinylated poly(propylacrylic acid) polymer.

A further aspect of the invention provides methods for obtaining cytoplasmic delivery of biotinylated cargo, comprising the step of exposing cells to a complex comprising (a) a fusion protein comprising a protein transduction domain linked to streptavidin to obtain cytoplasmic delivery of the biotinylated cargo, (b) a biotinylated cargo, and (c) a biotinylated endosomal releasing polymer.

The following examples illustrate representative embodiments now contemplated for practicing the invention, but should not be construed to limit the invention.

EXAMPLE 1

This Example describes studies showing that the membrane-traversing capability of the TAT peptide can be conferred upon the versatile streptavidin molecular adaptor protein. TAT-SA was assayed for its retention of biotin binding and also for its ability to translocate through the cell membrane of human Jurkat T-cells. Cellular uptake and intracellular distribution were monitored by fluorescence activated cell sorting (FACS), biological activity assays, and fluorescence microscopy of labeled TAT-SA. In addition, the ability of an endosomal-releasing polymer to enhance cytoplasmic delivery of internalized TAT-SA complexes was investigated.

Materials and Methods

Construction and Expression of TAT-Streptavidin Gene: The TAT-SA gene was constructed using core streptavidin (Chilkoti et al. (1995) *Proc. Natl. Acad Sci. U.S.A.* 92:1754-8) in pUC18 plasmid (New England Biolabs, Beverly, Mass.) and overhang-primer polymerase chain reaction (PCR). The following oligonucleotide primers were used: forward overhang (5' ACG GGG AAT CAT ATG TAC GGT CGT AAA AAA CGT CGT CAG CGT CGT CGT GGT GCT GAA GCT GGT ATC ACC 3', SEQ ID NO:42) and reverse (5' TTC GAA CCG TGA CCG GCA GC 3', SEQ ID NO:43) from Integrated DNA Technologies (Coralville, Iowa), where the bold text denotes the TAT sequence. The PCR-generated cassette was digested with NdeI and HindIII restriction endonucleases (New England Biolabs) and subsequently ligated into NdeI/HindIII-linearized pUC18. The ligation products were transformed into TOP10F' competent cells (Invitrogen, Carlsbad, Calif.) and successful production of the TAT-SA gene was confirmed by DNA sequencing with an ABI Prism BigDye Terminator Cycle Sequencing-Ready Reaction Kit (Perkin-Elmer, Boston, Mass.). The TAT-SA gene construct was subsequently subcloned into the pET21a (Invitrogen) expression vector and transformed into BL21 (DE3) cells (Novagen, Madison, Wis.) in preparation for large-scale expression. The TAT-SA construct in pET21a was expressed and purified as described previously (Klumb et al. (1998) *Biochemistry* 37:7657-63). Briefly, TAT-SA was expressed as insoluble inclusion bodies that were isolated and then dissolved in 6 M guanidine hydrochloride, followed by refolding via dilution into Tris buffer, pH 8.0. Refolded, functional protein was purified by affinity chromatography using a 2-iminobiotin agarose column (Sigma, St. Louis, Mo.). Protein concentrations were determined using an extinction coefficient of 34,000 $M^{-1}$ $cm^{-1}$/subunit. Characterization of the TAT-SA fusion protein included matrix-assisted laser desorption/ionization (MALDI) mass spectrometry, SDS-PAGE and biotin off-rate determination using [$^3$H]biotin (Amersham Biosciences, Piscataway, N.J.) according to previously described methods (Klumb et al. (1998) *Biochemistry* 37:7657-63).

Fluorescent Labeling: WT-SA and TAT-SA were labeled using Alexa Fluor 488 (Molecular Probes, Eugene, Oreg.). The fluorophore was dissolved in dimethylformamide at a concentration of 2 mg/ml and the conjugation reaction was performed with a 5-fold molar excess of the fluorophore in 0.1 M sodium carbonate-sodium bicarbonate, pH 9.0. The reaction was performed for 1 hour at room temperature, followed by dialysis with a 3500 MWCO Slide-A-Lyzer dialysis cassette (Pierce, Rockford, Ill.) in phosphate-buffered saline (PBS), pH 7.4. The protein concentration in the dialyzed sample was determined spectrophotometrically by subtracting $0.11 A_{495\ nm}$ of the fluorophore from the $A_{280\ nm}$ of the protein, using the tetramer WT-SA extinction coefficient of 136,000 $M^{-1}$ $cm^{-1}$. The degree of labeling was calculated by dividing the $A_{495\ nm}$ of the fluorophore by the molar concentration of the protein and the dye extinction coefficient of 71 000 $M^{-1}$ $cm^{-1}$. WT-SA and TAT-SA were successfully labeled with Alexa Fluor 488 with a degree of labeling of 1.63 and 2.68 fluorophores per tetramer, respectively.

Preparation of TAT-SA Complexes: TAT-SA was complexed with a biotinylated version of the 240 kDa fluorescent protein R-phycoerythrin (R-PE) (Molecular Probes) by incubation at varying molar ratios for 15 minutes at room temperature to provide TAT-SA:R-PE complexes. TAT-SA-alkaline phosphatase complexes were formed similarly using biotinylated calf intestinal alkaline phosphatase (AP) (Pierce) to examine the delivery of a large, active enzyme (140 kDa). For quenching studies, TAT-SA-AP complexes were formed under the same conditions with Alexa-488-labeled biotinylated calf intestinal AP (US Biological, Swampscott, Mass.) at a 1:2 molar ratio.

Cell Culture: Human Jurkat T-lymphoma cells were maintained in RPMI 1640 medium supplemented with 10% fetal bovine serum and 2 mM glutamine. Jurkat cells were grown on T75 tissue culture flasks to a density of $1\times10^6$ cells/ml before subculturing. Cells were incubated at 37° C. in a 5% carbon dioxide atmosphere.

Flow Cytometry: The internalization of fluorescently labeled TAT-SA, fluorescent TAT-SA-(R-PE) complexes, and fluorescent TAT-SA-AP complexes were analyzed in Jurkat cells which had been plated at a density of $10^5$ cells in 0.2 ml of RPMI medium in a 96-well microtiter plate. Triplicate protein samples were prepared in PBS, pH 7.4 and incubated at 37° C. in a 5% carbon dioxide atmosphere for 3 hours. The cells were then washed in 0.2 ml of PBS, pH 7.4 three times before resuspension in fresh buffer for analysis on a Coulter Epics FACS analyzer with excitation at 488 nm. TAT-SA-AP-treated cells were washed three times and then resuspended in PBS, pH 7.4 containing a 2·X equivalent of anti-Alexa Fluor 488 (Molecular Probes) at room temperature for 20 min, followed by FACS analysis. For each protein sample, data were collected for 10,000 events of the gated population and included forward scatter (FS), side scatter (SS), fluorescence- 1 (FL-1, Alexa Fluor 488) and fluorescence-2 (FL-2, (R)-phycoerythrin) measurements. In all analyses, viable cells were chosen based on FS and SS values, where cells displaying high FS and low SS were considered intact and uncompromised because of their light diffraction profiles. The number of viable cells considered positive for protein uptake was determined by gating cells with FL-1 greater than the maximum of control wells with no labeled protein added.

Alkaline Phosphatase Activity Assay: Jurkat cells were prepared as described above. Triplicate samples of unlabeled WT-SA-AP and TAT-SA-AP complexes were prepared at different molar ratios of AP, while holding the concentration of each SA species constant at 80 nM. Cells were treated and incubated at 37° C. in a 5% carbon dioxide atmosphere for 4 hours. The cells were then washed three times with PBS, pH 7.4 and resuspended in 0.1 ml of 1·X Reporter Lysis Buffer (RLB) (Promega, Madison, Wis.). Cell lysates were incubated at room temperature for 15 minutes with intermittent shaking and then centrifuged at 300 g for 5 minutes to sediment cellular debris and unlysed cells. Colorimetric reactions were initiated by pipetting 50 μl of the supernatant from each well into a fresh 96-well plate and subsequently adding 50 μl of 1-Step pNPP Buffer (Pierce). After incubating at 37° C. for 30 minutes, reactions were stopped by the addition of 150 μl of 1 M sodium carbonate and the absorbance at 405 nm was measured on a plate reader (SoftMax). Calibration curves were generated using a series of dilutions of biotinylated AP (Pierce) in PBS, pH 7.4 and 1·X Reporter Lysis Buffer (RLB) (Promega, Madison, Wis.).

Optical Microscopy: Jurkat cells were plated at a density of $10^5$ cells and incubated with 80 nM Alexa 488-labeled TAT-SA for 3 hours. Jurkat cells were washed three times, resuspended in 15 μl of PBS, pH 7.4, mounted on a glass slides for imaging using a confocal Leica TCS NT/SP on a DMIRBE inverted microscope. Images were acquired using a 100·X inverted oil immersion objective and the appropriate filter set for Alexa-488.

Preparation of Polymer Complexes: Amine-terminated poly(propylacrylic acid) (PPAA) was synthesized and end-biotinylated using sulfosuccinimidyl-6-(biotinamido)-6-hexanoate (EZ-Link Sulfo-NHS-LC-Biotin, Pierce) as described previously (Lackey et al. (1999) Bioconj. Chem. 10:401-5; Murthy et al. (1999) J. Control. Release 61:137-43; Lackey et al. (2002) Bioconj. Chem. 13:996-1001). The weight-average molecular weight of PPAA before biotinylation was 38 kDa and the biotinylation efficiency was determined to be approximately 100%. TAT-SA-PPAA complexes were assembled by mixing together the two components at a 1:1 molar ratio at room temperature for 15 minutes. SDS-PAGE was used to characterize the formation of the complexes.

Results and Discussion

Characterization of the TAT-SA Fusion Protein: MALDI mass spectrometry of refolded, purified TAT-SA yielded a molecular weight of 15,001.01 Da, which is in a good agreement with the calculated theoretical mass of 15,001.50 Da (ExPASy) per monomer. The biotin off-rate kinetics of TAT-SA were measured and compared with WT-SA to determine possible effects of the TAT sequence on the biotin-binding properties of the mutant. Biotin-bound WT- and TAT-SA displayed monoexponential, first-order dissociation kinetics. The first-order dissociation rate constant ($k_{off}$) for WT-SA and TAT-SA at 37° C. was found to be $25 \times 10^{-6}$ $s^{-1}$ and $30 \times 10^{-6}$ $s^{-1}$, respectively.

Internalization of TAT-SA and TAT-SA-(R-PE) Complexes: Flow cytometry was used to quantify the uptake of the Alexa-488-labeled TAT-SA and fluorescent TAT-SA-(R-PE) complexes. Test samples were compared with untreated cells and included cells incubated with WT-SA alone, WT-SA-(R-PE) complexes, TAT-SA alone or TAT-SA-(R-PE) complexes. Jurkat cells were incubated with a fixed 80 nM concentration of WT-SA or TAT-SA, each complexed with a varying molar ratio of R-PE as indicated. FACS analysis of washed cells 3 hours after treatment with TAT-SA revealed a strong Alexa-488 fluorescence signal (Table 3) compared with gated WTSA-treated cells, indicating that internalization was mediated by the NH2-terminal TAT peptide. Similar FACS results were obtained when transfections were performed at 37° C. or 4° C. Samples treated with TAT-SA-(R-PE) complexes at a 1:1 molar ratio displayed strong phycoerythrin fluorescence intensity, whereas those treated with WT-SA-(R-PE) did not (Table 3).

TABLE 3

Cellular Uptake of WT-SA and TAT-SA Complexes

| Treatment (t = 3 hr) | % R-PE-Positive Cells |
|---|---|
| None | 0.42 ± 0.03 |
| R-PE Only | 1.40 ± 0.40 |
| WT-SA:R-PE 1:1 | 5.33 ± 0.65 |
| TAT-SA:R-PE 1:1 | 95.77 ± 1.15 |

In order to differentiate between internalized and extracellular membrane-bound fluorescence, the same studies were conducted in the presence of an impermeable fluorescence quenching antibody directed against Alexa-488. The fraction of membrane-bound TAT-SA is statistically significant ($P<0.01$) yet only accounts for a slight shift in the overall fluorescence intensity of the treated cell population, as demonstrated in Table 4. The fluorescence intensity of WT-SA-treated cells, however, was not significantly affected by post-treatment with the fluorescence quenching antibody ($P>0.05$). This study confirmed that most of the cell-associated TAT-SA fluorescence was from internalized protein and not due to an extracellular membrane-bound fraction.

TABLE 4

FACS Analysis of Membrane-Bound WT-SA and TAT-SA Complexes

| | % TAT-SA-Positive Cells | |
|---|---|---|
| Treatment (t = 3 hr) | Without Quenching Antibody | With Quenching Antibody |
| None | 4.72 ± 0.66 | 6.10 ± 0.27 |
| WT-SA | 18.07 ± 1.20 | 12.06 ± 2.93 |
| TAT-SA | 61.03 ± 4.34 | 47.80 ± 1.85 |

Delivery of a Biologically Active Enzyme: TAT-SA complexes were formed with biotinylated calf intestinal AP which had been labeled with Alexa-488. Nearly 85% of cells treated with TAT-SA-AP complexes were positive for Alexa-488 fluorescence as compared with about 8% of cells treated with WT-SA-AP complexes (Table 5). Post-treatment of parallel cell populations with the impermeable quenching antibody resulted in a slight, statistically insignificant ($P>0.05$) decrease in the fluorescence intensity of gated cells, indicating again that a majority of the detected fluorescence signal was due to internalized TAT-SA-AP complexes.

TABLE 5

FACS Analysis of Membrane-Bound TAT-SA-AP and WT-SA-AP complexes

| Treatment (t = 4 hr) | % AP-Positive Cells | |
|---|---|---|
| | Without Quenching Antibody | With Quenching Antibody |
| None | 3.59 ± 0.85 | 5.04 ± 0.31 |
| AP only | 6.19 ± 1.94 | 10.83 ± 3.36 |
| WT-SA-AP 1:2 | 5.73 ± 0.47 | 8.68 ± 4.02 |
| TAT-SA-AP 1:2 | 86.73 ± 3.78 | 83.00 ± 1.66 |

AP activity was measured in the cellular lysates of TAT-SA-AP-treated cells 4 hours after treatment. Enzymatic activity increased with increasing molar ratio of AP, illustrating the ability for one TAT-SA molecule to bind and internalize multiple AP molecules with no apparent loss of enzymatic function (Table 6). WT-SA-AP conjugates were not internalized and the treated samples displayed an amount of activity consistent with the negative controls. These data confirmed that TAT-SA is capable of delivering a large biotinylated enzyme (140 kDa) with retention of biological activity.

TABLE 6

Delivery of Alkaline Phosphatase (AP) With TAT-SA

| Treatment | AP activity (milliunits) |
|---|---|
| None | 0.10 ± 0.00 |
| AP only | 0.43 ± 0.00 |
| WT-SA-AP 1:1 | 1.65 ± 0.18 |
| TAT-SA-AP 1:1 | 10.31 ± 1.24 |

Intracellular Distribution of Internalized TAT-SA and TAT-SA Complexes: The intracellular localization of internalized TAT-SA was investigated through the use of confocal microscopy and fluorescently labeled TAT-SA and TAT-SA-polymer complexes. Confocal images of live Jurkat cells 3 hours after treatment with Alexa-488-labeled TAT-SA were examined. WT-SA-treated cells showed low or no fluorescence, consistent with low-level, non-specific uptake, whereas cells treated with TAT-SA displayed punctate patches of intracellular fluorescence. These results reveal that the TAT sequence does not direct cytoplasmic delivery in this streptavidin fusion protein. The punctate fluorescence distribution is strongly suggestive of endosomal/lysosomal compartmentalization. The strongly positive TAT sequence likely directs macromolecular pinocytosis of electrostatically bound TAT-SA, which would result in endosomal/lysosomal localization.

Figure 2:
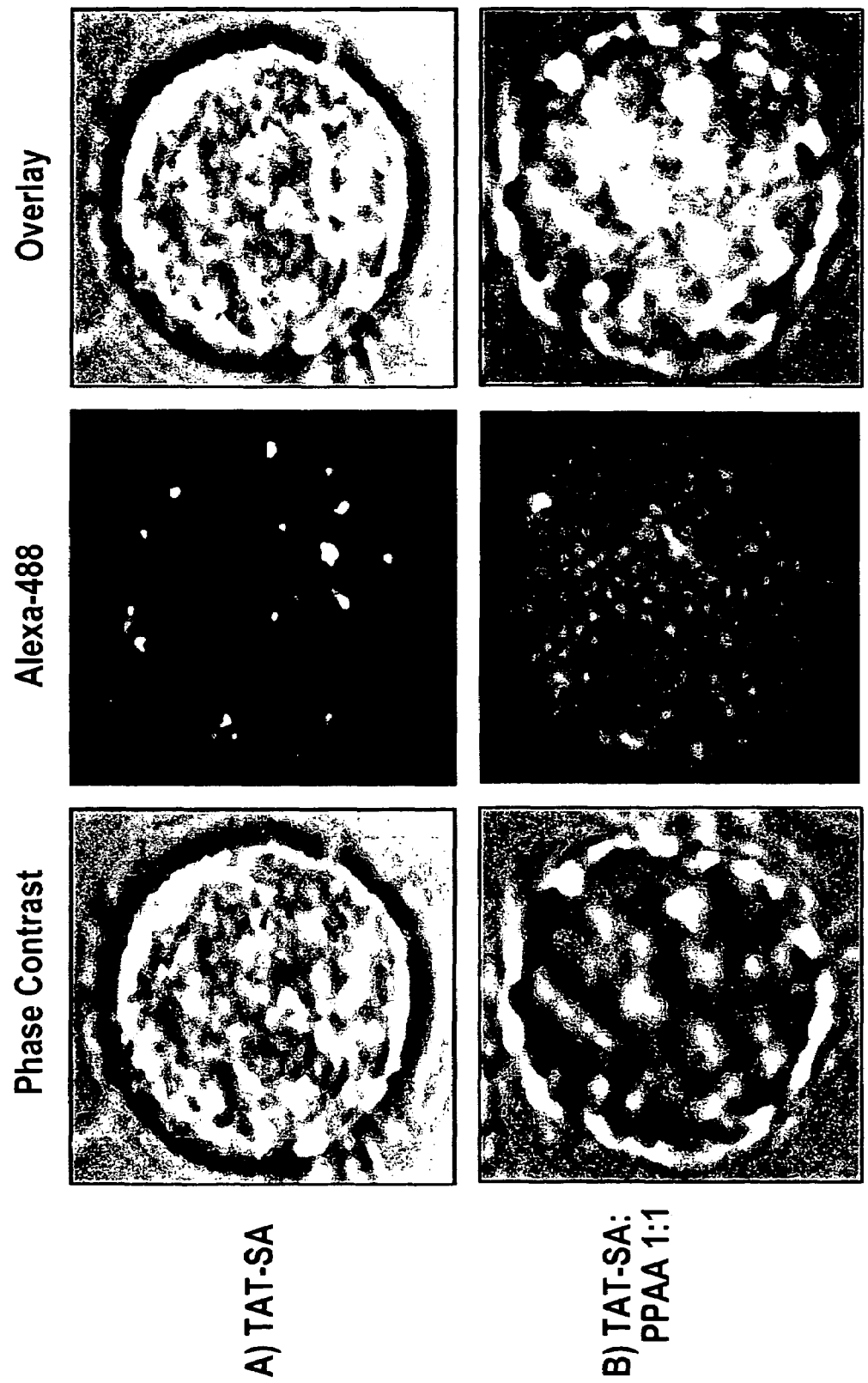
FIGS. 2A and B show confocal images of live Jurkat T-cells 3 hours after treatment with Alexa-labeled TAT-SA complexes (FIG. 2A) or TAT-SA:PPAA complexes (FIG. 2B), as described in EXAMPLE 1.

In many cases it is desirable to deliver protein cargo into the cytoplasm. It has been previously shown that PPAA is capable of directing endosomal release of biomolecules at the low-ered-pH environment found in endosomes and lysosomes (Lackey et al. (1999) *Bioconj. Chem.* 10:401-5; Lackey et al. (2002) *Bioconj. Chem.* 13:996-1001; Murthy et al. (1999) *J. Control. Release* 61:137-43). The ability of PPAA to enhance cytoplasmic delivery of TAT-SA was therefore investigated. Representative confocal images of single cells 4 hours after treatment with fluorescently labeled TAT-SA-PPAA complexes are shown in FIG. 2B. Jurkat cells incubated in the absence of PPAA showed mostly punctate fluorescence, consistent with endocytotic uptake (FIG. 2A). The cells treated with TATSA-PPAA complexes were characterized by a very diffuse fluorescence distribution (FIG. 2B), suggesting PPAA-mediated endosomal release of the complexes.

Recent findings have suggested that TAT-mediated entry may be based on constitutive endocytic processes, such as those involved in the recycling of cell-surface proteins or through a caveolar endocytic mechanism (Leifert et al. (2002) *Gene Ther.* 9:1422-8; Fittipaldi et al. (2003) *J. Biol. Chem.* 278:34141-9; Leifert & Lindsay Whitton (2003) *Mol. Ther.* 8:13-20; Lundberg et al. (2003) *Mol. Ther.* 8:143-50; Richard et al. (2003) *J. Biol. Chem.* 278:585-90; Vives et al. (2003) *Curr. Protein Pept. Sci.* 4:125-32). As suggested in a recent review, the TAT peptide may be better classified as a cationic reagent similar to existing cationic transfection reagents, including PEI, poly-L-lysine and DOTAP (Leifert & Lindsay Whitton (2003) *Mol. Ther.* 8:13-20). Other studies have presented convincing data on live cells that seem to show the effective delivery of active protein species into the cytoplasmic compartment (Nagahara et al. (1998) *Nat. Med.* 4:1449-52; Kwon et al. (2000) *FEBS Lett.* 485:163-7; Jo et al. (2001) *Nat. Biotechnol.* 19:929-33; Xia et al. (2001) *Nat. Biotechnol.* 19:640-4; Cao et al. (2002) *J. Neurosci.* 22:5423-31; Joshi et al. (2002) *Genesis* 33:48-54; Kabouridis et al. (2002) *J. Immunol.* 169:2587-93; Peitz et al. (2002) *Proc. Natl. Acad. Sci. USA.* 99:4489-94).

The data presented in this Example demonstrate that the TAT-SA fusion does not function/act through a truly transductive process, but instead directs internalization through an electrostatically mediated cell surface adherence. As confirmed through live cell microscopy, the TAT-SA fusion protein is internalized with high efficiency but sequestered in small vesicular compartments, suggestive of an endocytic mode of entry. The internalization of TAT-SA complexed to a range of biotinylated cargo proteins gave similar results. In order to achieve cytoplasmic delivery, the biomimetic, pH-sensitive polymer PPAA was used to direct endosomal release. The addition of the biotinylated PPAA to TAT-SA significantly altered the intracellular distribution of the internalized fusion protein and cargo, resulting in diffuse cytoplasmic localization. This demonstrates that TAT-SA and PPAA can be used jointly as a biomolecular vehicle for delivering heterogeneous cargo proteins of large size in an apparent stepwise uptake and endosomal release mechanism.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A composition, comprising a complex formed between (a) a fusion protein comprising a protein transduction domain linked to streptavidin (b) a biotinylated cargo for intracellular delivery and (c) a (propylacrylic acid)-containing polymer.

2. The composition of claim 1, wherein the protein transduction domain comprises the protein transduction domain of the Human Immunodeficiency Virus type 1 (HIV-1) TAT protein.

3. The method of claim 1, wherein the (propylacrylic acid)-containing polymer is poly(propylacrylic acid).

4. The composition of claim 1, wherein the (propylacrylic acid)-containing polymer is biotinylated.

5. A method for obtaining intracellular delivery of biotinylated cargo, comprising the step of exposing cells to a complex comprising (a) a fusion protein comprising a protein transduction domain linked to streptavidin to obtain intracellular delivery of the biotinylated cargo (b) a biotinylated cargo and (c) a (propylacrylic acid)-containing polymer.

6. The method of claim 5, wherein the protein transduction domain comprises the protein transduction domain of the HIV-1 TAT protein.

7. The method of claim 5, wherein the (propylacrylic acid)-containing polymer is biotinylated.

8. A method for obtaining cytoplasmic delivery of biotinylated cargo, comprising the step of exposing cells to a complex comprising (a) a fusion protein comprising a protein transduction domain linked to streptavidin to obtain cytoplasmic delivery of the biotinylated cargo, (b) a biotinylated cargo, and (c) a biotinylated (propylacrylic acid)-containing polymer.

9. The method of claim 8, wherein the (propylacrylic acid)-containing polymer is poly(propylacrylic acid).

10. The method of claim 9, wherein the protein transduction domain comprises the protein transduction domain of the HIV-1 TAT protein.

* * * * *

UNITED STATES PATENT AND TRADEMARK OFFICE
CERTIFICATE OF CORRECTION

| | | |
|---|---|---|
| PATENT NO. | : 7,534,819 B2 | Page 1 of 1 |
| APPLICATION NO. | : 11/150588 | |
| DATED | : May 19, 2009 | |
| INVENTOR(S) | : B. Albarran et al. | |

It is certified that error appears in the above-identified patent and that said Letters Patent is hereby corrected as shown below:

COLUMN    LINE

32            15          "claim 9," should read --claim 8,--
(Claim 10,  line 1)

Signed and Sealed this

Twenty-seventh Day of October, 2009

David J. Kappos
*Director of the United States Patent and Trademark Office*